United States Patent [19]
Greene

[11] Patent Number: 5,299,736
[45] Date of Patent: Apr. 5, 1994

[54] AIR FRESHENER DEVICE WITH A CERAMIC CONTAINER AND AN ABSORBENT PAD

[76] Inventor: John Greene, 36 Arran Drive, Suite 220, St. Catharines, Ontario, Canada, L2N 6S5

[21] Appl. No.: 70,114
[22] Filed: May 17, 1993
[51] Int. Cl.$^5$ ............................................. A61L 9/12
[52] U.S. Cl. ......................................... 239/56; 239/34; 239/211
[58] Field of Search ..................... 239/34, 53, 55, 56, 239/211, 44, 51.5, 54

[56] References Cited

U.S. PATENT DOCUMENTS

| | | | |
|---|---|---|---|
| 366,693 | 7/1887 | Sherman | 239/55 X |
| 1,889,075 | 11/1932 | Mills | 239/55 |
| 2,218,037 | 10/1940 | Duers et al. | 239/54 |
| 3,679,133 | 7/1972 | Sekiguchi et al. | 239/34 |
| 4,389,446 | 6/1983 | Blom et al. | 239/51.5 X |
| 4,958,768 | 9/1990 | Ishihara | 239/34 |
| 5,161,680 | 11/1992 | Badgley | 239/51.5 X |
| 5,178,839 | 1/1993 | Spector . | |
| 5,242,111 | 9/1993 | Nakoneczny | 239/44 |

FOREIGN PATENT DOCUMENTS 8404459 11/1984 World Int. Prop. O. ............ 239/34

*Primary Examiner*—Andres Kashnikow
*Assistant Examiner*—William Grant
*Attorney, Agent, or Firm*—Marks & Clerk

[57] ABSTRACT

An air freshener device, comprising a container with porous ceramic walls defining a closed internal space, a closure member for selectively permitting access to and sealing the internal space, and a replaceable absorbent pad the absorbent pad being impregnated with a fragrant substance adapted for insertion into the internal space so as to occupy only a portion thereof and release fragrant vapors into the internal space at a controlled rate. The released fragrant vapors first build up within the internal space and then diffuse through the porous walls of the container for release into the atmosphere.

5 Claims, 1 Drawing Sheet 5,299,736

AIR FRESHENER DEVICE WITH A CERAMIC CONTAINER AND AN ABSORBENT PAD

BACKGROUND OF THE INVENTION

This invention relates to an air freshener device, and more particularly to a figurine of aesthetically pleasing appearance capable of releasing fragrant vapors into the atmosphere.

Many types of air freshener are on the market. These range from aerosol type sprays to scented devices that are adapted to release fragrant vapors into the atmosphere.

U.S. Pat. No. 4,889,284 discloses a rechargeable air freshener in which a figurative form includes a body and a head section, and an outer casing of permeable material. The interior of the casing is filled with a compressible core of absorbent material having good wicking properties. However, in this device the interior space is filled with absorbent material, which is directly in contact with the fabric walls. As the result, the outer walls are subject to staining, and furthermore excessive rates of evaporation are experienced, especially under warm conditions.

An object of the invention is to provide an improved air freshener device.

SUMMARY OF THE INVENTION

According to the present invention there is provided an air freshener device, comprising a container with porous ceramic walls defining a closed internal space, a closure member for selectively permitting access to and sealing said internal space, and a replaceable absorbent pad, said absorbent pad being impregnated with a fragrant substance adapted for insertion into said internal space so as to occupy only a portion and release fragrant vapors into said internal space at a controlled rate, whereby said released fragrant vapors first build up within said internal space and then diffuse through the porous walls of the container for release into the atmosphere.

In a preferred embodiment, the container is in the form of an aesthetically pleasing figurine, made of a white porous ceramic material, such as bisque. The absorbent pad is in the form of a felt or blotter inserted through a hole in the base of the figurine, the hole being subsequently closed by a plastic or rubber cap.

It is an important feature of the invention that the container have porous ceramic walls and that the absorbent pad does not fill the internal space. Furthermore, the fragrant substance should not be in free-flowing liquid form, since such a substance tends to wick up the porous walls of the container and leave an unpleasant stain.

In the inventive device, the fragrant substance first releases vapors into the internal space of the container. These vapors build up to an equilibrium concentration and diffuse through the porous ceramic walls. The two-stage process, whereby the vapors first build up within the internal space to a relatively high concentration and then gradually diffuse through the walls of the container leads to a much more satisfactory, slow release of fragrance into the atmosphere than was possible with the prior art. Unlike the prior art, the fragrant substance first contacts the porous walls in to vapor phase after having been released from the absorbent pad within the internal space.

BRIEF DESCRIPTION OF THE DRAWINGS

The invention will now be described in more detail, by way of example only, with reference to the accompanying drawings in which.

DESCRIPTION OF THE PREFERRED EMBODIMENTS

Figure 1:
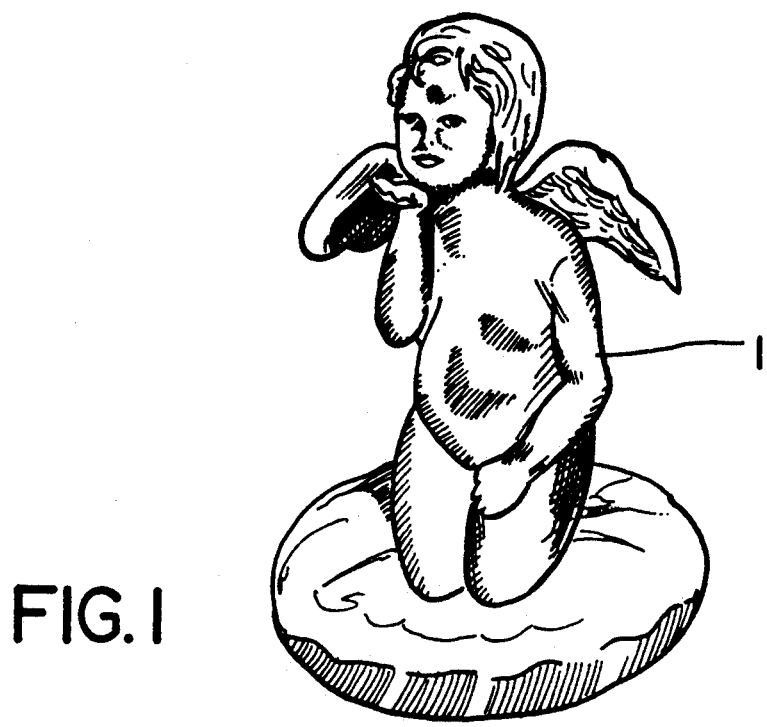
FIG. 1 is a perspective view of an air freshener in accordance with the invention.
Figure 2:
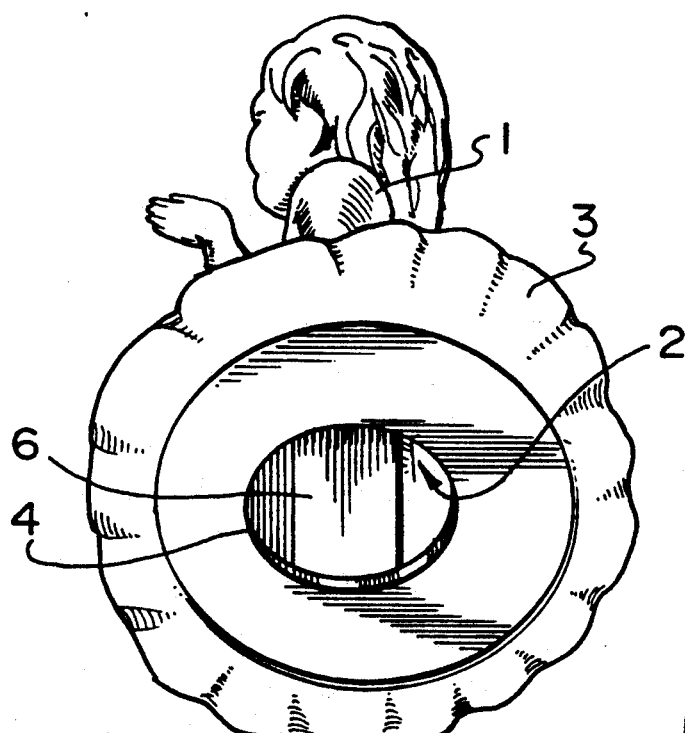
FIG. 2 is an underneath view of the air freshener in accordance with the invention.
Figure 3:
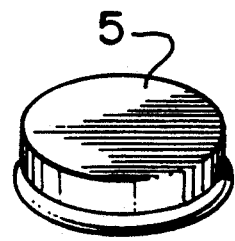
FIG. 3 is perspective view of a plug for closing the internal space within the air freshener.

Referring to the drawings, the air freshener comprises a figurine 1 in the form of an angel kneeling on a cloud and blowing a kiss. The figurine 1 is made of a white porous ceramic material, known as bisque. This is normally an intermediate product in the manufacture of ceramics. The figurine is hollow inside to define an internal space 2 (FIG. 2). Base 3, which forms the cloud, has a planar bottom portion with a central aperture 4 closable by a rubber or plastic plug 5.

Within the internal space 2 is freely located a small rectangular absorbent pad 6 in the form of a wick, which is free to move within the internal space 2. The pad 6 is made of a controlled release paper and impregnated with an essential oil, such that the essence is slowly released from the pad at a controlled rate. In use, the plug 5 closes the aperture 4 to confine the pad 6 within the space 2.

In an alternative embodiment, the absorbent pad 6 can be mounted directly on the plug 5 so as to prevent it coming into contact with the porous walls of the figurine 1. However, minimal point contact is acceptable since such contact does not substantially effect the operation of the inventive device.

In use, the user inserts an impregnated pad 6 through the aperture 4 into the internal space of the figurine 1. After the user has pushed the plug 5 into the aperture 4, the pad 6 becomes trapped in the internal space 2 and fragrant vapors are gradually released from the absorbent pad 6 at a controlled rate.

It is an important feature of the invention that these vapors can first build up to a relatively high concentration within the internal space 2. These concentrated vapors then gradually diffuse through the porous walls of the figurine 1 so that the figurine gives off a pleasing scent. When the strength of the scent diminishes below an acceptable level, the user merely removes the plug 5 to replace the pad 6.

Relative to the prior art, the described device ensures a desirably slow, relatively constant rate of emission of scent. The effect of the pad, which causes a controlled release into the internal space of the figurine 1, and the subsequent diffusion through the walls of the figurine 1, is to ensure a gradual effusion into the atmosphere of the fragrance. This gradual effusion is subtle and is not overpowering on the initial charge as was so often the case with the prior art.

Since this device is intended to be aesthetically pleasing, the absence of oil stains is also a particularly desirable feature. Indeed, porous walls can act as a form of chromatographic substrate, causing the components of an oil-based scent to separate and leave a most unsightly mark if a liquid is employed, or liquid flows directly from the wick to the walls of the container, as for example in the prior art patent referred to above.

The use of the absorbent pad is also desirable because the absence of liquid that might otherwise be consumed by children.

The fragrant substance can be any suitable fragrance, for example for a Pot Pourri, comprising a concentration of scent with an appropriate release agent. Suitable fragrances are available on the market, and one such fragrance would be an essential oil manufactured by Scentex, of Toronto, Ontario.

I claim:

1. An air freshener device, comprising a container with porous ceramic walls defining a closed internal space, a closure member for selectively permitting access to and sealing said internal space, and a replaceable absorbent pad, said absorbent pad being impregnated with a fragrant substance adapted for insertion into said internal space so as to occupy only a portion thereof and release fragrant vapors into said internal space at a controlled rate, whereby said released fragrant vapors first build up within said internal space and then diffuse through the porous walls of the container for release into the atmosphere.

2. An air freshener device as claimed in claim 1, wherein said container is in the form of a figurine.

3. An air freshener device as claimed in claim 1, wherein said container is made of bisque.

4. An air freshener device as claimed in claim 1, wherein said closure member is a plug, and said absorbent pad is freely located within said space.

5. An air freshener device as claimed in claim 1, wherein said absorbent pad comprises a controlled release paper.

* * * * *